United States Patent
Nishizawa

(10) Patent No.: US 10,330,801 B2
(45) Date of Patent: Jun. 25, 2019

(54) RADIATION DETECTOR, MEDICAL IMAGE DIAGNOSIS APPARATUS, DETECTOR PACKAGE, SCINTILLATOR ARRAY, SCINTILLATOR ARRAY MANUFACTURING METHOD, AND RADIATION DETECTOR MANUFACTURING METHOD

(71) Applicant: Canon Medical Systems Corporation, Otawara-shi (JP)

(72) Inventor: Kazuto Nishizawa, Yokohama (JP)

(73) Assignee: Canon Medical Systems Corporation, Otawara-shi (JP)

( * ) Notice: Subject to any disclaimer, the term of this patent is extended or adjusted under 35 U.S.C. 154(b) by 0 days.

(21) Appl. No.: 15/921,872

(22) Filed: Mar. 15, 2018

(65) Prior Publication Data
US 2018/0267183 A1   Sep. 20, 2018

(30) Foreign Application Priority Data
Mar. 17, 2017   (JP) .................................. 2017-052354

(51) Int. Cl.
| G01T 1/20 | (2006.01) |
| H01L 27/146 | (2006.01) |
| H01L 25/00 | (2006.01) |
| A61B 6/00 | (2006.01) |
| G01T 7/00 | (2006.01) |
| G01T 1/28 | (2006.01) |

(52) U.S. Cl.
CPC .............. *G01T 1/28* (2013.01); *A61B 6/4208* (2013.01); *G01T 1/2002* (2013.01); *G01T 1/2018* (2013.01); *G01T 7/00* (2013.01); *H01L 25/50* (2013.01); *H01L 27/14663* (2013.01)

(58) Field of Classification Search
CPC ....... A61B 6/4208; G01T 1/2018; G01T 1/28; G01T 7/00; H01L 25/50; H01L 27/14663
See application file for complete search history.

(56) References Cited

U.S. PATENT DOCUMENTS 7,692,156 B1 * 4/2010 Nagarkar .............. G01T 1/1644
250/361 R

FOREIGN PATENT DOCUMENTS

| JP | 06-160538 | 6/1994 |
| JP | 2010-139383 | 6/2010 |

* cited by examiner

*Primary Examiner* — Mark R Gaworecki
(74) *Attorney, Agent, or Firm* — Oblon, McClelland, Maier & Neustadt, L.L.P.

(57) ABSTRACT

A radiation detector according to an embodiment includes a photodiode array and a scintillator array. The photodiode array has a plurality of active areas arranged in a grid formation. The scintillator array is laminated on the photodiode array, is configured to emit light in response to incidence of radiation thereto, and has a plurality of modification parts that do not penetrate therethrough, in regions each corresponding to a position between two of the active areas, for a purpose of preventing crosstalk.

17 Claims, 18 Drawing Sheets

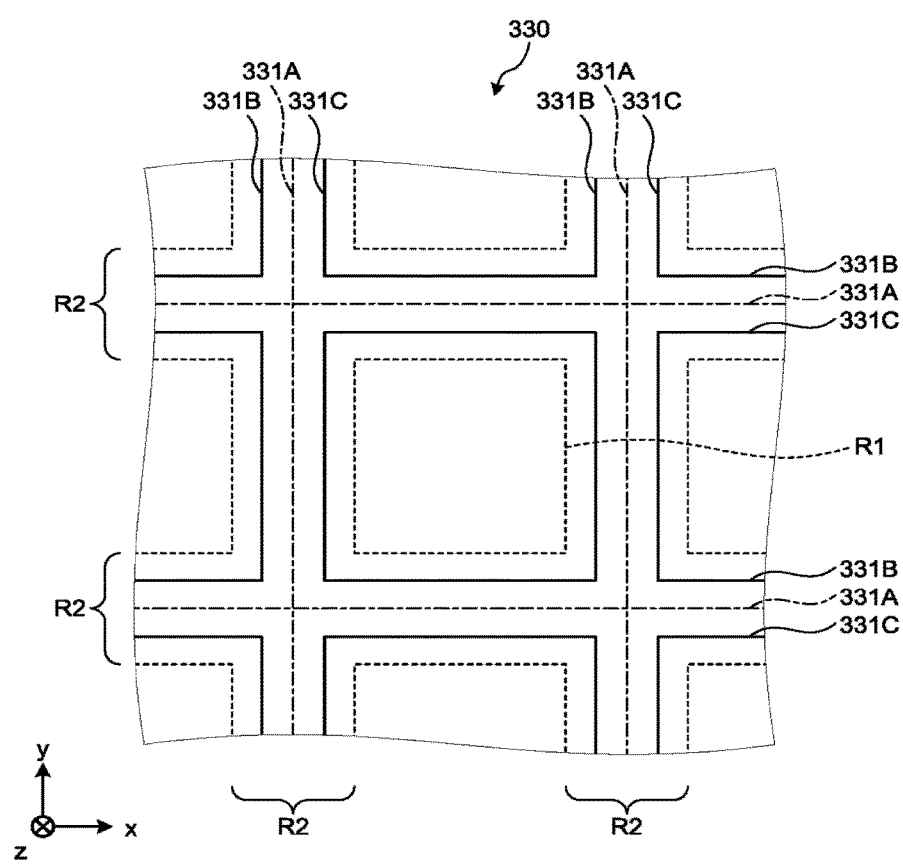

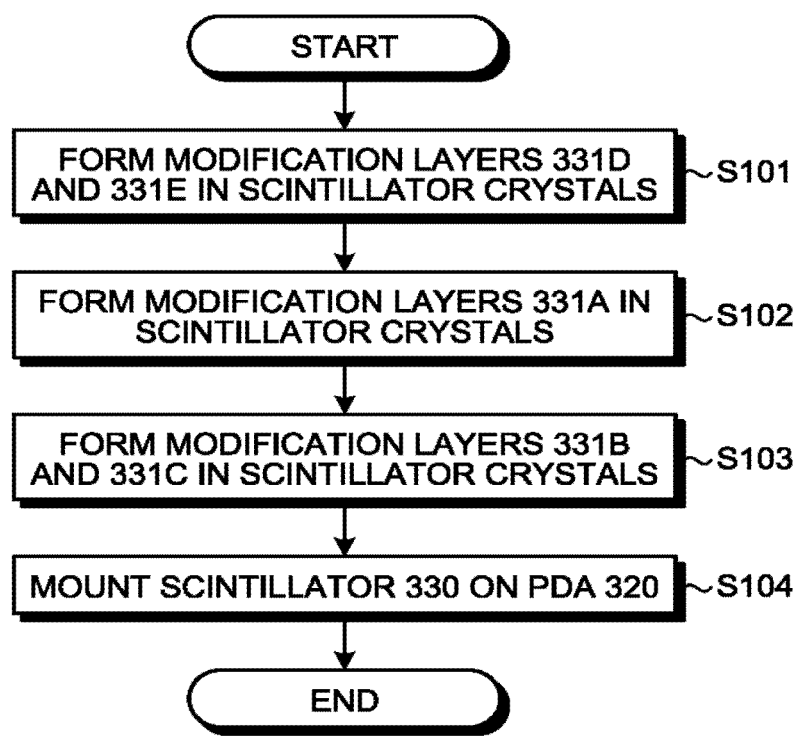

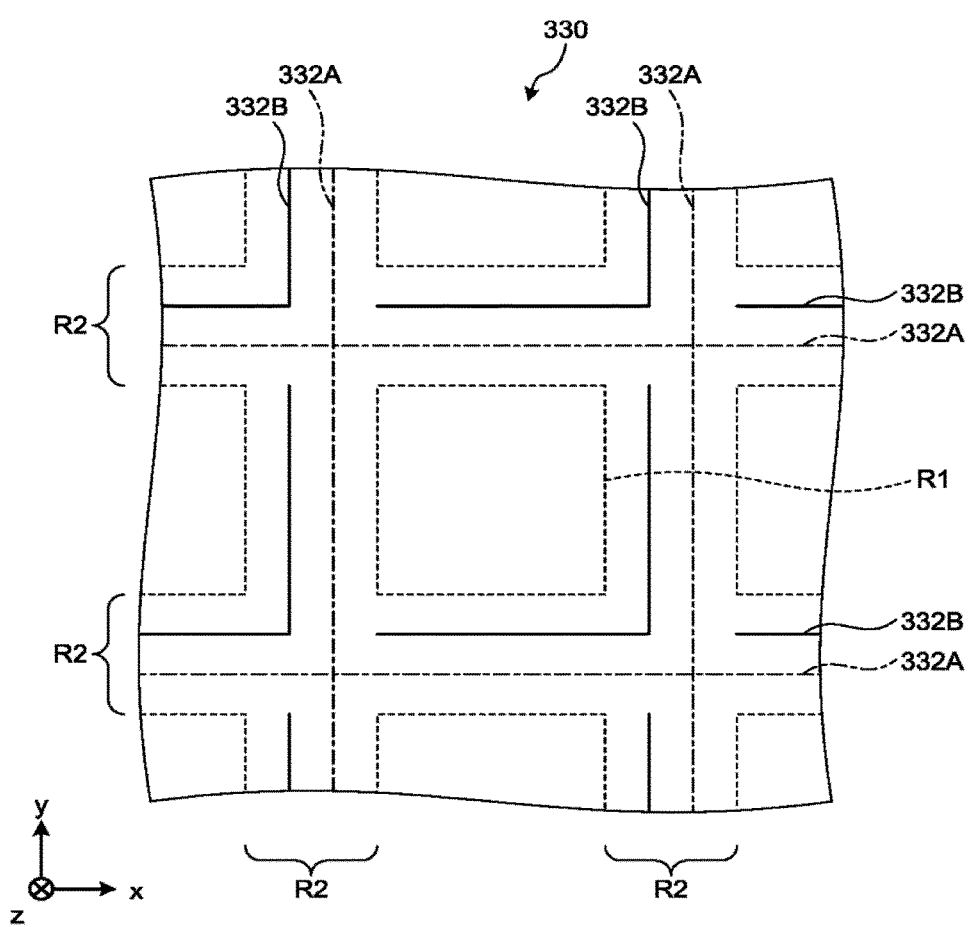

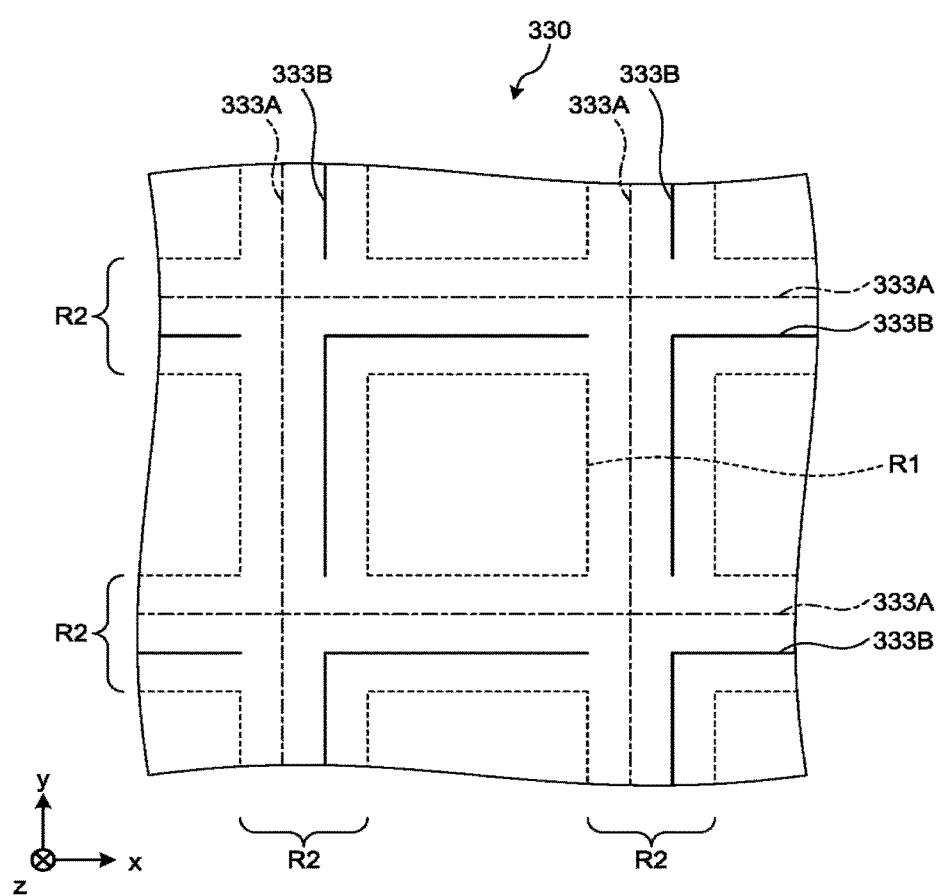

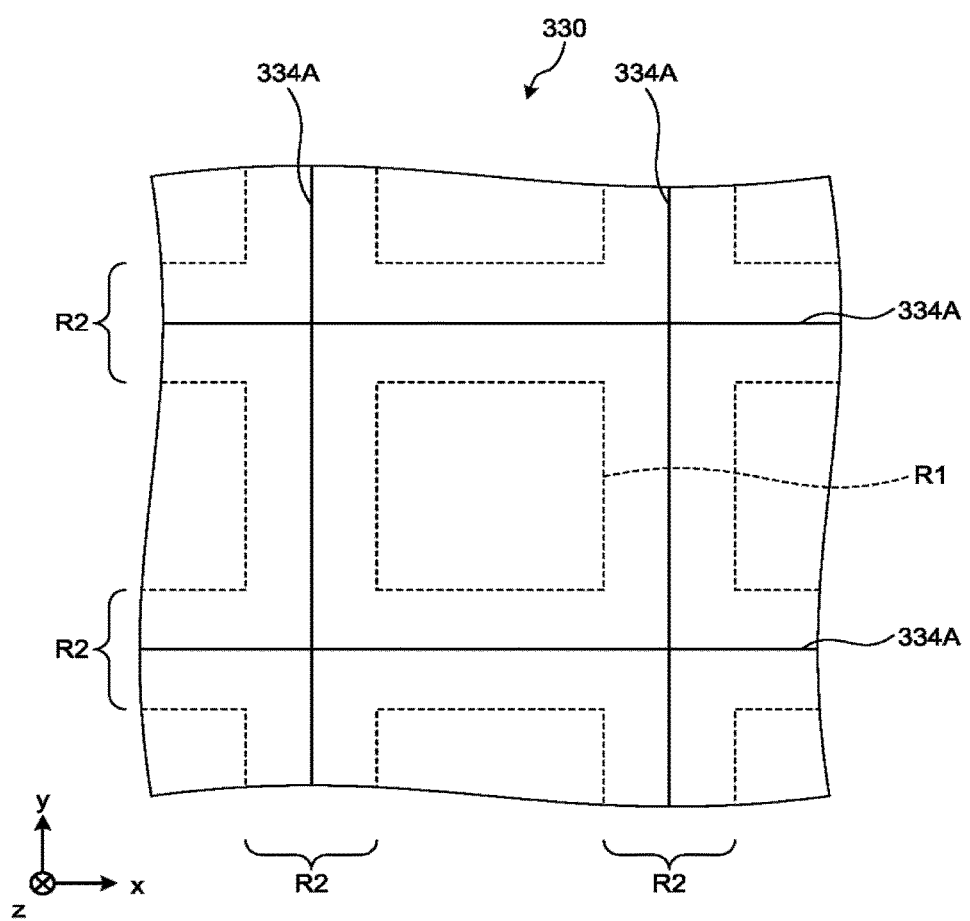

RADIATION DETECTOR, MEDICAL IMAGE DIAGNOSIS APPARATUS, DETECTOR PACKAGE, SCINTILLATOR ARRAY, SCINTILLATOR ARRAY MANUFACTURING METHOD, AND RADIATION DETECTOR MANUFACTURING METHOD

CROSS-REFERENCE TO RELATED APPLICATIONS

This application is based upon and claims the benefit of priority from Japanese Patent Application No. 2017-052354, filed on Mar. 17, 2017; the entire contents of which are incorporated herein by reference.

FIELD

Embodiments described herein relate generally to a radiation detector, a medical image diagnosis apparatus, a detector package, a scintillator array, a scintillator array manufacturing method, and a radiation detector manufacturing method.

BACKGROUND

Conventionally, medical image diagnosis apparatuses configured to generate a medical image of an examined subject by using radiation are known, including X-ray Computed Tomography (CT) apparatuses, Positron Emission Tomography (PET) apparatuses, Single Photon Emission Computed Tomography (SPECT) apparatuses, and gamma cameras, among others. Such medical image diagnosis apparatuses include a radiation detector configured to detect radiation such as X-rays or γ-rays.

The radiation detector includes a scintillator array configured to emit light (scintillation light) in response to radiation becoming incidence thereto; and a Photodiode Array (PDA) configured to output electrical signals in accordance with the scintillation light. The scintillator array and the PDA function in units of a plurality of detecting elements arranged in a channel direction and a slice direction. A plurality of scintillator arrays and a plurality of PDAs are installed in a radiation detector in the form of detector packages, each of which is a unit that can be replaced when a failure occurs.

Each of the scintillator arrays has partition walls that are formed in a grid formation in a planar view and is divided into units corresponding to a plurality of detecting elements by the partition walls. For example, the partition walls are formed by using a material obtained by sandwiching an aluminum evaporated layer between white polyethylene terephthalate (PET) sheets or reflective material resin such as a white adhesive agent including resin and white particles. To form the partition walls with scintillator crystals by using the reflective material resin, generally speaking, the following steps are performed: forming grooves on the scintillator crystals, impregnating the grooves with the reflective material resin and hardening the reflective material resin, and grinding the rear surface.

BRIEF DESCRIPTION OF THE DRAWINGS

FIGS. 5A and 5B are drawings illustrating an example of a structure of the scintillator array according to the first embodiment;

FIG. 6 is a flowchart illustrating an example of a manufacturing method of the X-ray detector according to the first embodiment;

FIGS. 7A and 7B are drawings illustrating an example of a structure of a scintillator array according to a first modification example of the first embodiment;

FIGS. 8A and 8B are drawings illustrating an example of a structure of a scintillator array according to a second modification example of the first embodiment;

FIGS. 10A and 10B are drawings illustrating an example of a structure of a scintillator array according to a fourth modification example of the first embodiment;

DETAILED DESCRIPTION

It is an object of the present disclosure to provide a radiation detector, a medical image diagnosis apparatus, a detector package, a scintillator array, a scintillator array manufacturing method, and a radiation detector manufacturing method that have high reliability.

A radiation detector according to an embodiment includes a photodiode array and a scintillator array. The photodiode array has a plurality of active areas arranged in a grid formation. The scintillator array is laminated on the photodiode array, is configured to emit light in response to incidence of radiation, and has a plurality of modification parts that do not penetrate therethrough, in regions each corresponding to a position between two of the active areas, for a purpose of preventing crosstalk.

Exemplary embodiments of a radiation detector, a medical image diagnosis apparatus, a detector package, a scintillator array, a scintillator array manufacturing method, and a radiation detector manufacturing method will be explained below, with reference to the accompanying drawings.

In the embodiments described below, examples will be explained in which the disclosed techniques are applied to an X-ray Computed Tomography (CT) apparatus; however, possible embodiments are not limited to these examples. For instance, the disclosed techniques are widely applicable to medical image diagnosis apparatuses configured to generate a medical image of an examined subject by using radiation, such as Positron Emission Tomography (PET) apparatuses, Single Photon Emission Computed Tomography (SPECT) apparatuses, and gamma cameras, among others. Further, it is possible to realize the disclosed techniques as a radiation detector provided for a medical image diagnosis apparatus. Further, it is possible to variously realize the disclosed techniques not only for medical purposes, but also in a radiation detector or the like configured to detect an amount of radiation in the environment (the atmosphere), for example.

First Embodiment

Figure 1:
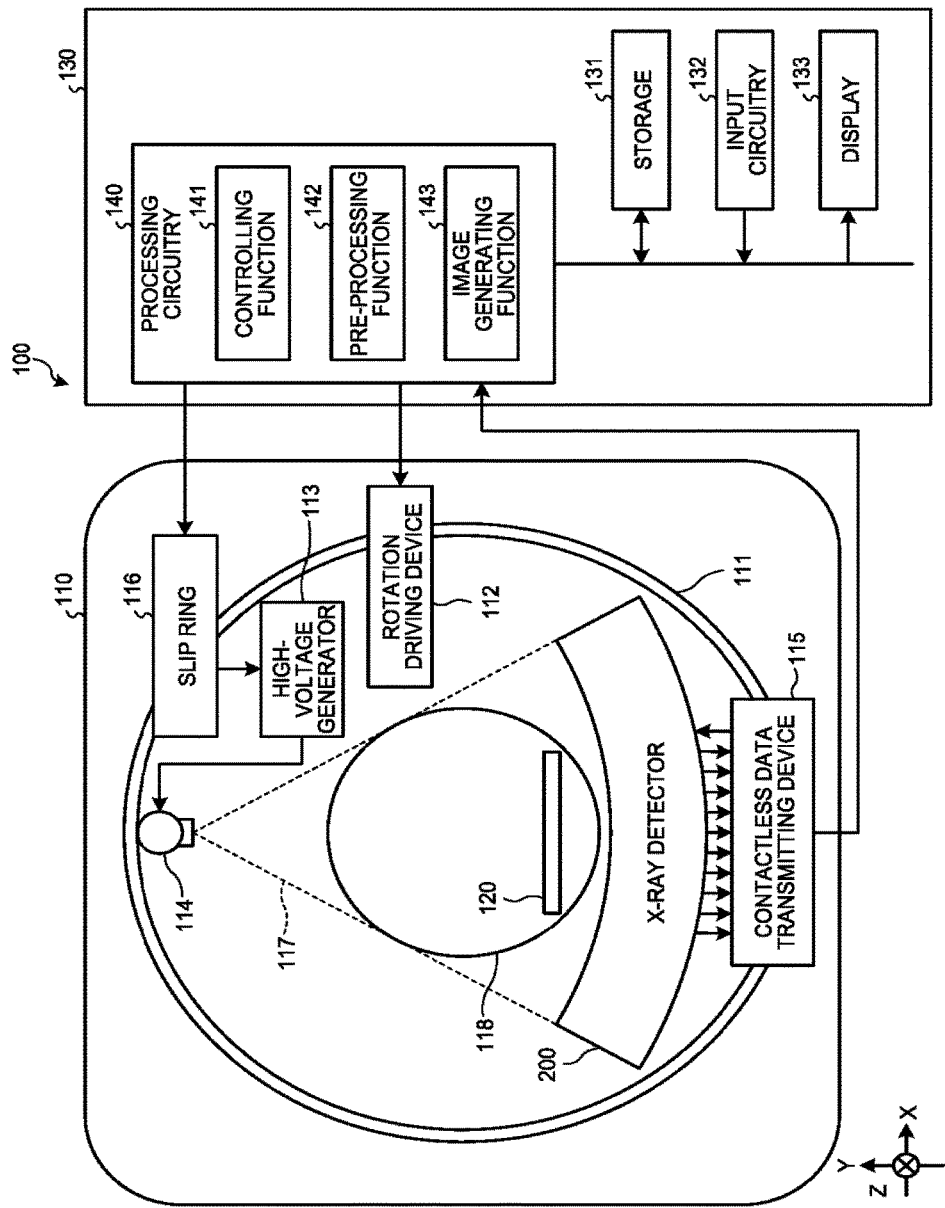
FIG. 1 is a diagram illustrating an exemplary configuration of an X-ray CT apparatus according to a first embodiment.

An exemplary configuration of an X-ray CT apparatus according to a first embodiment will be explained, with reference to FIG. 1. FIG. 1 is a diagram illustrating an exemplary configuration of the X-ray CT apparatus according to the first embodiment. As illustrated in FIG. 1, for example, an X-ray CT apparatus 100 according to the first embodiment includes a gantry 110, a couchtop 120, and a console device 130.

The gantry 110 houses therein a rotation supporting mechanism including a rotating frame 111, a rotation driving device 112, and a frame supporting mechanism. The rotating frame 111 has installed thereon a high-voltage generator 113, an X-ray generating device 114, an X-ray detector 200, and a contactless data transmitting device 115. Further, the gantry 110 is set with a coordinate system based on X-, Y-, and Z-axes. The X-axis corresponds to the horizontal direction of the gantry 110. The Y-axis is an axis orthogonal to the X-axis and corresponds to the vertical direction of the gantry 110. The Z-axis is an axis orthogonal to the X-axis and the Y-axis and corresponds to the direction of the rotation axis of the rotating frame 111 in a non-tilted state.

The rotating frame 111 is an annular frame (a supporting member) configured to support the X-ray generating device 114 and the X-ray detector 200. The rotating frame 111 is supported by the frame supporting mechanism so as to be rotatable on the Z-axis set with the gantry 110.

The rotation driving device 112 is configured to drive the rotation of the rotating frame 111. For example, the rotation driving device 112 is structured with a driving mechanism including a motor and an actuator, or the like.

Under control of processing circuitry 140, the high-voltage generator 113 is configured to generate an X-ray tube voltage to be applied to the X-ray generating device 114 and an X-ray tube current to be supplied to the X-ray generating device 114, by using electric power supplied thereto from the outside of the gantry 110 via a slip ring 116. The high-voltage generator 113 is configured by using, for example, an electric circuit including a transformer and a rectifier, or the like. Alternatively, the high-voltage generator 113 may be installed on the outside of the gantry 110. In that situation, the high-voltage generator 113 is configured to apply the X-ray tube voltage to the X-ray generating device 114 and to supply the X-ray tube current to the X-ray generating device 114, via the slip ring 116.

The X-ray generating device 114 is a device configured to generate X-rays. The X-ray generating device 114 is structured by using, for example, an X-ray tube (a vacuum tube) configured to receive a supply of high voltage from the high-voltage generator 113 and to emit thermo electrons from the negative pole (which may be called a filament) to the positive pole (a target). A plurality of collimator plates are attached to an X-ray radiation window provided in the front face of the X-ray generating device 114. The collimator plates are configured to arrange X-rays radiated from an X-ray focal point into a cone beam shape (a quadrangular pyramid shape). In FIG. 1, the radiation range of the X-rays is indicated with broken lines 117. As indicated with the broken lines 117, the X-rays are radiated onto the inside of an opening 118 formed around the center of the rotating frame 111 of the gantry 110.

The X-ray detector 200 is configured to detect X-rays that have passed through an examined subject (hereinafter "patient"). For example, the X-ray detector 200 has such a structure that a plurality of rows of X-ray detecting elements are arranged in a slice direction, while each row of X-ray detecting elements includes a plurality of X-ray detecting elements that are arranged in the channel direction along one arc centered on the focal point of the X-ray generating device 114. The plurality of X-ray detecting elements arranged in the two directions in this manner are configured to detect the X-rays that were emitted from the X-ray generating device 114 and have passed through a patient P and are each configured to output an electrical signal corresponding to an amount of X-rays to a Data Acquisition System (DAS) substrate 221. The DAS substrate 221 includes an amplifier configured to perform an amplifying process on the electrical signals and an Analog/Digital (A/D) converter configured to convert the electrical signals to digital signals. The DAS substrate 221 is configured to generate detection data (raw data) from the electrical signals output from the X-ray detecting elements. The raw data generated by the DAS substrate 221 is transferred to the console device 130 by the contactless data transmitting device 115. Details of the DAS substrate 221 will be explained later.

The contactless data transmitting device 115 is a communication device capable of transmitting data in a contactless manner, by using a magnetic signal, an optical signal, or the like. The contactless data transmitting device 115 is configured to transmit the raw data output from the X-ray detector 200 to a pre-processing function 142.

The couchtop 120 is a plate-like member on which the patient is placed. The couchtop 120 can be moved by a couchtop driving device (not illustrated) along the X-axis, the Y-axis, and the Z-axis. Under control of the processing circuitry 140, the couchtop driving device moves the couchtop 120 to the inside of the opening 118 formed in the gantry 110. The couchtop driving device is either a motor or an actuator configured to move the couchtop 120.

As illustrated in FIG. 1, the console device 130 includes storage 131, input circuitry 132, a display 133, and the processing circuitry 140.

The storage 131 stores therein various types of data. For example, the storage 131 stores therein projection data medical images generated by the processing circuitry 140. For example, the storage 131 is realized by using a semiconductor memory element such as a Random Access Memory (RAM), a flash memory, or the like, a hard disk, an optical disk, or the like.

The input circuitry 132 is configured to receive various types of input operations from the operator, to convert the received input operations into electrical signals, and to transmit the electrical signals to the processing circuitry 140. For example, the input circuitry 132 receives, from the operator, an acquisition condition used when projection data is acquired, a reconstruction condition used when a CT image is reconstructed, an image processing condition used when a processed image is generated from a CT image, and the like. For example, the input circuitry 132 is realized by using a mouse, a keyboard, a trackball, a switch, a button, a joystick, and/or the like.

The display 133 is configured to output various types of information. For example, the display 133 is configured to output a medical image generated by the processing circuitry 140, a Graphical User Interface (GUI) used for receiving various types of operations from the operator, and the like.

For example, the display 133 is realized by using a liquid crystal panel, a Cathode Ray Tube (CRT) monitor, or the like.

The processing circuitry 140 is configured control overall operations of the X-ray CT apparatus 100 in accordance with the electrical signals of the input operations transmitted thereto from the input circuitry 132.

For example, the processing circuitry 140 includes a controlling function 141, the pre-processing function 142, and an image generating function 143. For example, the processing circuitry 140 is realized by using a processor.

On the basis of the acquisition condition received from the operator via the input circuitry 132, the controlling function 141 is configured to acquire the projection data of the patient, by controlling the rotation driving device 112, the high-voltage generator 113, the couchtop driving device, and the like.

The pre-processing function 142 is configured to generate the projection data by performing a pre-processing process on the raw data transmitted thereto from the contactless data transmitting device 115 and to store the generated projection data into the storage 131. For example, the pre-processing function 142 performs a pre-processing process such as a logarithmic converting process, an offset correcting process, a sensitivity correcting process between the channels, a beam hardening correcting process, and/or the like.

The image generating function 143 is configured to generate a medical image of the patient on the basis of the X-rays detected by the X-ray detector 200 and to store the generated medical image into the storage 131.

More specifically, the image generating function 143 reconstructs a CT image of the patient by performing a reconstructing process on the projection data generated by the pre-processing function 142, on the basis of the reconstruction condition transmitted thereto from the input circuitry 132. For example, the image generating function 143 reconstructs a three-dimensional image (volume data) by implementing a Feldkamp method, a cone beam reconstruction method, or the like. As another example, the image generating function 143 reconstructs a two-dimensional image (a tomographic image) by performing a back projection process while implementing a fan beam reconstruction method, a Filtered Back Projection (FBP) method, or the like.

Further, the image generating function 143 is configured to generate various types of processed images by performing various types of image processing processes on the data of the CT image, on the basis of the image processing condition transmitted thereto from the input circuitry 132. For example, the image generating function 143 generates a projection image such as a Multi Planar Reconstruction (MPR) image, a Maximum Intensity Projection (MIP) image, or the like, or a volume rendering image, or the like.

In this situation, for example, the controlling function 141, the pre-processing function 142, and the image generating function 143 included in the processing circuitry 140 are each recorded in the storage 131 in the form of a computer-executable program. The processing circuitry 140 is a processor configured to realize the functions corresponding to the computer programs (hereinafter, "programs"), by reading the programs from the storage 131 and executing the read programs. In other words, the processing circuitry 140 that has read the programs corresponding to the functions has the controlling function 141, the pre-processing function 142, and the image generating function 143 illustrated within the processing circuitry 140 in FIG. 1.

Further, the example in FIG. 1 illustrates the situation in which the controlling function 141, the pre-processing function 142, and the image generating function 143 included in the processing circuitry 140 are realized by the single processor; however, possible embodiments are not limited to this example. For instance, the functions included in the processing circuitry 140 may be realized as being distributed among, or integrated together into, two or more processors or a single processor, as appropriate.

The term "processor" used in the above explanation denotes, for example, a Central Processing Unit (CPU), a Graphical Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). The one or more processors realize the functions thereof by reading the programs stored in a storage circuit and executing the read programs. Instead of storing the programs into the storage circuit, it is also acceptable to directly incorporate the programs into the circuits of the one or more processors. In that situation, the one or more processors realize the functions thereof by reading the programs incorporated in the circuit thereof and executing the read programs. The processors in the first embodiment do not each necessarily have to be structured as a single circuit. It is also acceptable to structure one processor by combining together a plurality of independent circuits so as to realize the functions thereof.

Figure 2:
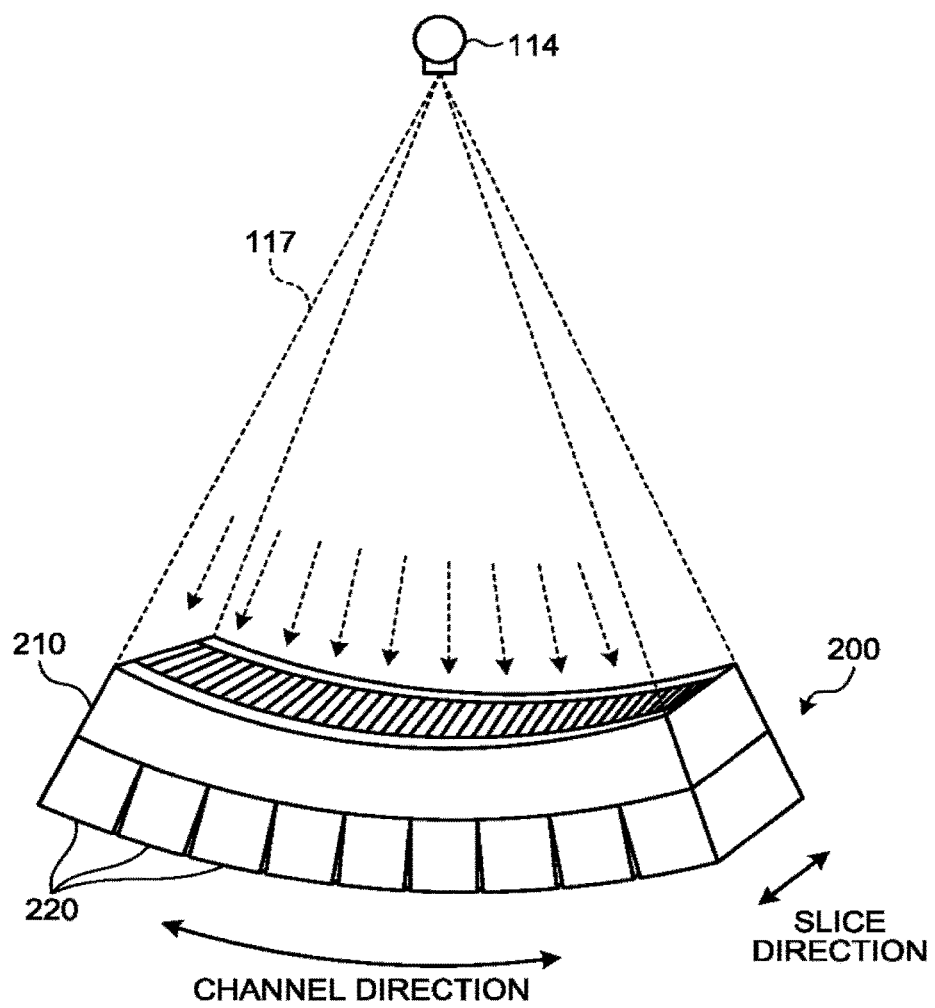
FIG. 2 is a drawing illustrating an exemplary configuration of an X-ray detector according to the first embodiment.

An exemplary configuration of the X-ray detector 200 according to the first embodiment will be explained, with reference to FIG. 2. FIG. 2 is a drawing illustrating an exemplary configuration of the X-ray detector 200 according to the first embodiment. For example, as illustrated in FIG. 2, the X-ray detector 200 includes a collimator unit 210 and a plurality of detector modules 220. In FIG. 2, the X-ray radiation directions are indicated by the arrows with broken lines. Further, in the explanations below, the circumferential direction centered on the X-ray generating device 114 will be referred to as the channel direction. The direction extending along the Z-axis, which is the rotation axis of the rotating frame 111 described above, will be referred to as the slice direction.

The collimator unit 210 is configured to eliminate scattered rays from the X-rays that are incident to the detector module 220. More specifically, the collimator unit 210 is formed substantially in an arc shape centered on the X-ray generating device 114 and is disposed before the detector modules 220 in terms of the X-ray radiation directions. For example, the collimator unit 210 is structured by attaching a plurality of collimator plates, along the X-ray radiation directions, to a supporting member formed to have an arc shape along the channel direction.

The plurality of detector modules 220 are arranged along the channel direction on the outer circumferential side of the collimator unit 210. FIG. 2 illustrates the example in which the plurality of detector modules 220 are arranged in a one-dimensional manner along the channel direction; however, possible embodiments are not limited to this example. For instance, the detector modules 220 may be arranged in a two-dimensional manner along the channel direction and the slice direction.

Figure 3:
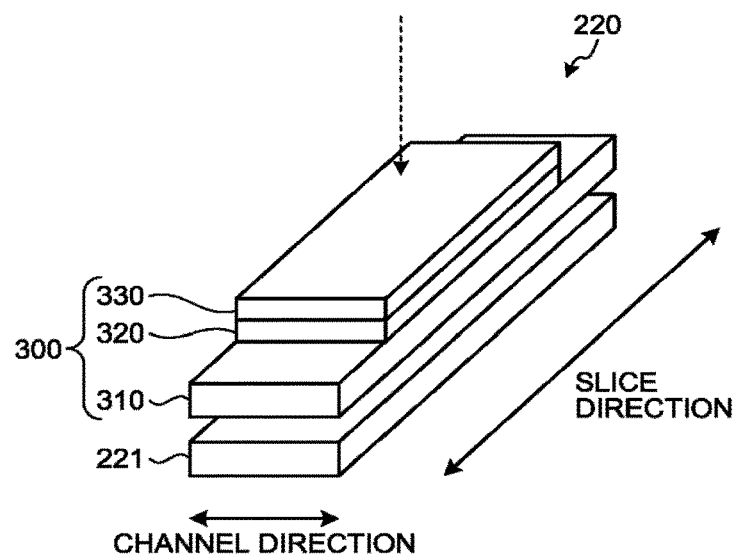
FIG. 3 is a drawing illustrating an exemplary configuration of a detector module according to the first embodiment.

An exemplary configuration of each of the detector modules 220 according to the first embodiment will be explained, with reference to FIG. 3. FIG. 3 is a drawing illustrating an exemplary configuration of the detector module 220 according to the first embodiment. In FIG. 3, the X-ray radiation direction is indicated by the arrow with a broken line.

As illustrated in FIG. 3, for example, the detector module 220 includes the Data Acquisition System (DAS) substrate 221, and a detector package 300. The detector package 300 includes a plate 310, a Photodiode Array (PDA) 320, and a scintillator array 330.

The DAS substrate 221 is configured to generate the raw data by performing the amplifying process, the A/D conversion process, and/or the like on X-ray intensity distribution data detected by the detector package 300 and to output the generated raw data. The DAS substrate 221 is supported within the detector module 220 by a supporting member (not illustrated). Further, between the DAS substrate 221 and the detector package 300, an X-ray blocking plate may be provided for the purpose of preventing an impact caused by direct incidence of X-rays.

The plate 310 is a member configured to support the PDA 320 and the scintillator array 330. The PDA 320 and the scintillator array 330 are adhered by using a transparent adhesive agent (e.g., an adhesive sheet). The adhesive agent may be one that is curable by Ultraviolet (UV) rays or heat. Any type of adhesive agent is applicable as long as the adhesive agent can be hardened.

The PDA 320 is formed by using, for example, a Silicon (Si) wafer. In accordance with energy of the light (scintillation light) generated by the scintillator array 330, the PDA 320 is configured to convert the scintillation light into electrical signals.

The scintillator array 330 is formed by scintillator crystals that emit light in response to incidence of X-rays thereto. For example, the scintillator array 330 generates light (scintillation light) in an amount corresponding to the energy of the X-rays that have become incident thereto via the collimator unit 210. Examples of the material that can be used for the scintillator crystals include GSO (Gd2SiO5:Ce), BGO (Bi4Ge3O12), LSO (Lu2SiO5:Ce), and garnet-based materials such as Lutetium Aluminum Garnet (LuAGr) and Yttrium Gallium Garnet (YGG).

In this situation, the X-rays that become incident to the scintillator array 330 is converted into scintillation light in each of the regions of the scintillator crystals divided by a partition wall layer in a grid formation.

Further, the scintillation light is converted into electrical signals in each of the sensitive regions (hereinafter, "active areas") of the PDA 320 corresponding to the regions divided by the partition wall layer. In other words, each of the scintillator crystals and active areas corresponding to a different one of the regions divided by the partition wall layer functions as one detecting element.

As explained above, each of the detector modules 220 is formed by arranging the DAS substrate 221 and the detector package 300 into a module. With this arrangement, for example, when a failure has occurred in one of the plurality of detector packages 300, it is possible to replace the failed detector package 300 in units of modules. In the present explanation, the example is explained in which the DAS substrate 221 and the detector package 300 are arranged to be in the form of the module; however, possible embodiments are not limited to this example. For instance, it is also acceptable to arrange the detector package 300, the DAS substrate 221, and the collimator unit 210 to be in the form of a module, by dividing the collimator unit 210 into sections corresponding to the detector packages 300. Also in that situation, it is possible to replace a failed detector package 300 in units of modules.

Further, in the first embodiment, the example is explained in which the X-ray detector 200 is provided with the DAS substrates 221; however, possible embodiments are not limited to this example. For instance, the DAS substrates 221 may be provided on the outside of the X-ray detector 200. In that situation, the DAS substrates 221 may be installed with either gantry 110 or the console device 130.

Although the configuration of the one detector module 220 is explained with reference to FIG. 3, each of the detector modules 220 installed on the X-ray detector 200 has the same configuration. In other words, in the X-ray detector 200, a plurality of detector packages 300 are arranged in the predetermined direction (e.g., the channel direction).

Figure 4:
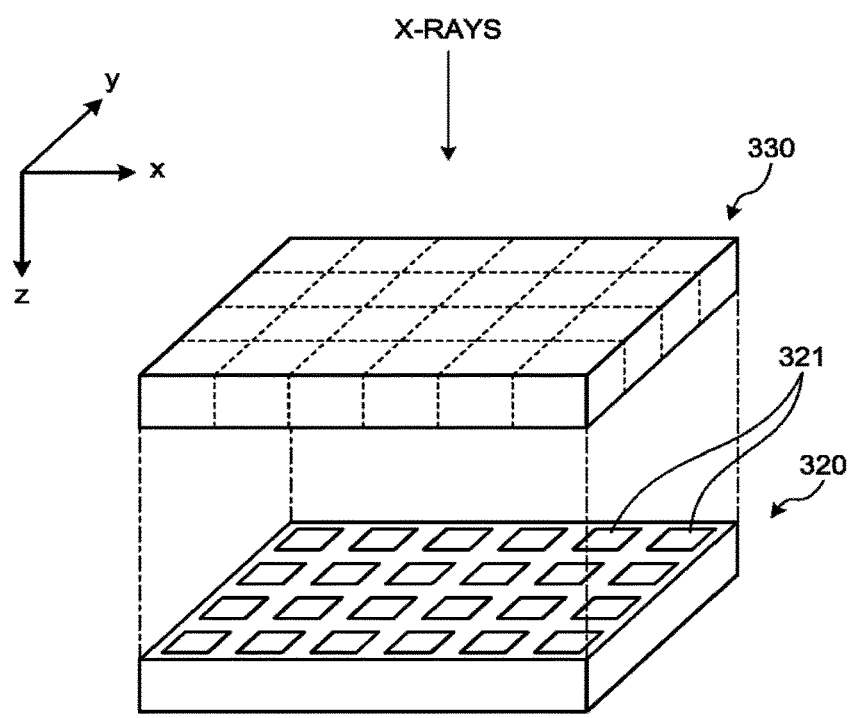
FIG. 4 is a drawing illustrating an exemplary configuration of a scintillator array according to the first embodiment.

An exemplary configuration of the scintillator array 330 according to the first embodiment will be explained, with reference to FIG. 4. FIG. 4 is a drawing illustrating the exemplary configuration of the scintillator array 330 according to the first embodiment. In FIG. 4, the X-ray radiation direction is indicated by the arrow with a solid line. Further, in the xyz coordinate system in FIG. 4, the x-direction corresponds to the channel direction, while the y-direction corresponds to the slice direction, and the z-direction corresponds to the X-ray radiation direction.

As illustrated in FIG. 4, the scintillator array 330 is formed with the scintillator crystals and is divided into the plurality of regions by the partition wall layer (corresponding to the broken line parts in the scintillator array 330 in FIG. 4) arranged in a grid formation. The regions divided by the partition wall layer arranged in the grid formation are provided in the positions corresponding to the plurality of active areas 321 of the PDA 320. In the example illustrated in FIG. 4, the PDA 320 includes 24 active areas 321 in total that are arranged in rows of six active areas extending in the x-direction and rows of four active areas extending in the y-direction. In correspondence with the 24 active areas 321, the scintillator array 330 is divided into 24 regions in total that are arranged in rows of six regions extending in the x-direction and rows of four regions extending in the y-direction.

It is explained above that the scintillator array 330 is divided by the partition wall layer arranged in the grid formation. It is indicated that the scintillator array 330 has a structure in which leakage of scintillation light between the detecting elements is inhibited by the partition wall layer arranged in the grid formation. In other words, it is indicated that the scintillator array 330 is functionally divided so as to function as the detecting elements and does not necessarily have to be divided into sections materially. The structure of the partition wall layer will be explained in detail later.

The configuration illustrated in FIG. 4 is merely an example, and possible embodiments are not limited to the illustrated example. For example, although FIG. 4 illustrates the example in which the scintillator array 330 is divided into the sections that are arranged in the rows of six sections extending in the x-direction and the rows of four sections extending in the y-direction, possible embodiments are not limited to this example.

Figure 5A:
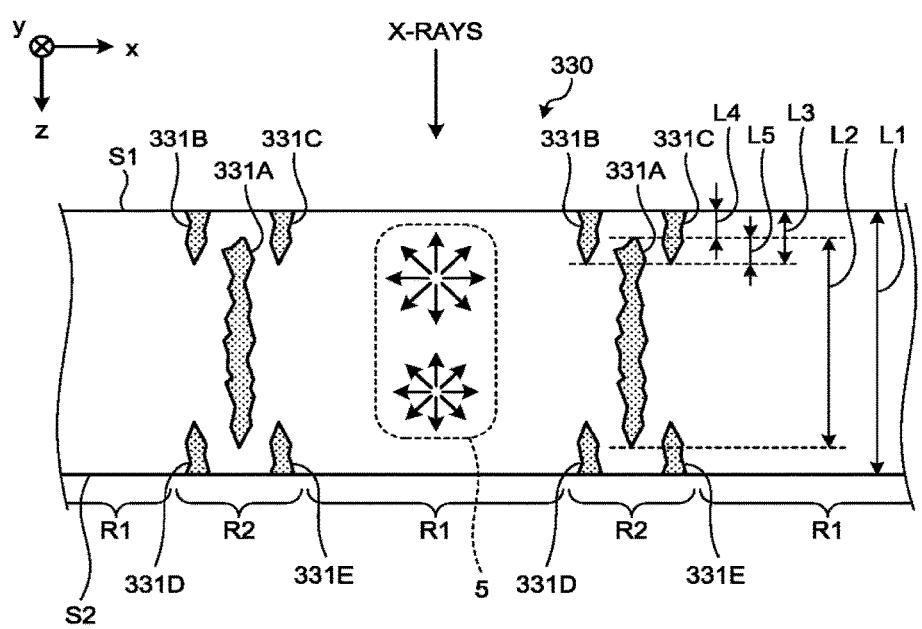

A structure of the scintillator array 330 according to the first embodiment will be explained, with reference to FIGS. 5A and 5B. FIGS. 5A and 5B are drawings illustrating an example of the structure of the scintillator array 330 according to the first embodiment. FIG. 5A illustrates the structure on an x-z cross-sectional plane of the scintillator array 330, in the xyz coordinate system of the scintillator array 330 illustrated in FIG. 4. FIG. 5B illustrates the structure of the scintillator array 330 viewed from the y-direction, in the xyz coordinate system of the scintillator array 330 illustrated in FIG. 4. In other words, FIG. 5A corresponds to a view (a lateral view) from a direction intersecting the incidence direction of the X-rays. FIG. 5B corresponds to a view (a planar view) from the incidence direction of the X-rays. In this situation, although FIG. 5A illustrates the x-z cross-sectional plane of the scintillator array 330 as an example, a y-z cross-sectional plane of the scintillator array 330 also has the same structure. Further, in FIG. 5A, the X-ray radiation direction is indicated by the arrow with a solid line. In the following sections, the incidence plane through which the X-rays become incident will be referred to as a "plane S1", whereas the exit plane through which scintillation light 5 exits to the active areas 321 will be referred to as a "plane S2". The distance between the plane S1 and the plane S2 will be expressed as "L1".

As illustrated in FIGS. 5A and 5B, the scintillator array 330 has a plurality of regions R1 respectively corresponding to the plurality of active areas 321 and a plurality of regions R2 each corresponding to a position between two of the plurality of active areas 321. The regions R1 and the regions R2 denote regions that are divided functionally. In other words, the regions R1 are regions that, together with the active areas 321, function as the detecting elements. Usually, in the scintillator array 330, as many regions R1 as the quantity of the active areas 321 are formed. For example, each of the regions R1 has a size (an area) to cover a corresponding one of the active areas 321 in a planar view and corresponds to a region having the shape of a quadrangular prism that is defined by the plane S1 and the plane S2. The regions R2 are regions that function as the partition wall layer to inhibit leakage (crosstalk) of the scintillation light 5 between the detecting elements. For example, the regions R2 are formed in a grid formation in a planar view to separate the regions R1 from one another (FIG. 5B). Each of the regions R2 is formed between two regions R1 that are positioned adjacent to each other and corresponds to a region defined by the plane S1 and the plane S2 (FIG. 5A). The regions R2 correspond to the positions of the broken lines of 330 in FIG. 4.

In this situation, to inhibit the crosstalk between the detecting elements, the scintillator array 330 according to the first embodiment has a plurality of modification layers formed in the regions R2. For example, the modification layers are each an aggregation of very small cracks. For example, the modification layers are formed by applying high energy to the inside of the scintillator crystals by having laser light concentrated on the inside thereof so that the scintillator crystals locally sublime. Alternatively, the modification layers may be formed by arranging certain parts to have optical characteristics that are different from those of the base material, as a result of melting or changing the quality of the certain parts. The refractive index of each of the modification layers formed in this manner is different from that of the scintillator crystals. For this reason, the modification layers are able to efficiently reflect the scintillation light 5.

It should be noted, however, that because the modification layers are for example each formed as the aggregation of the very small cracks in the scintillator crystals, the modification layers make scintillator crystals structurally fragile. For example, the scintillator array 330 needs to be mounted on the PDA 320 during a manufacturing step. For this reason, it is desirable to arrange the scintillator array 330 to have enough strength to endure manipulations during the manufacturing step.

Thus, the scintillator array 330 has modification layers 331A, 331B, 331C, 331D, and 331E. The modification layers 331A, 331B, 331C, 331D, and 331E are provided in mutually-different positions in each of the regions R2. Further, in a planar view, the modification layers 331A are formed in a grid formation, whereas the modification layers 331B, 331C, 331D, and 331E are each formed substantially in the shape of an L. In the following sections, when being referred to without being distinguished from another, the modification layers 331A, 331B, 331C, 331D, and 331E will collectively be referred to as "modification layers 331". Because the modification layers 331 are regions in which very small cracks and/or base material segments of which the quality has changed aggregate partially within the scintillator crystals, the modification layers 331 may be referred to as "modification parts" or "modification regions".

The modification layer 331A is provided substantially at the center of each of the regions R2 in terms of the x-direction, so as not to be continuous with the plane S1 or the plane S2. More specifically, each of the modification layers 331A has a length of L2 (where L2<L1) in the y-direction. Further, each of the modification layers 331A is provided in a position apart from each of the planes S1 and S2 by a distance L4. It is desirable to arrange L4 to be as short as possible within such a range that ensures enough strength to endure manipulations during the manufacturing step.

The modification layers 331B and 331C are provided on either side of each of the modification layers 331A in terms of the x-direction, so as to be continuous with the plane S1.

More specifically, it is desirable to form each of the modification layers 331B and the modification layers 331C to be positioned apart from the corresponding one of the modification layers 331A in terms of the x-direction and to be positioned as close as possible to the corresponding one of the modification layers 331A within such a range that ensures enough strength to endure manipulations during the manufacturing step. Further, each of the modification layers 331B and the modification layers 331C has a length L3 in the z direction. Simply forming the modification layers 331B and 331C is effective because the possibility that the scintillation light 5 may be reflected on the plane S1 and leak is being lowered thereby; however, it is desirable to arrange the length L3 to be a certain length. For example, the length L3 may be approximately twice as long as L4. Possible lengths of L3 are not limited to the example above. When L3 is longer than L4, it is possible to further reduce the leakage. In this configuration, the modification layer 331B and the modification layer 331C overlap with the modification layer 331A in a lateral view. The length of the overlap is expressed as L5.

The modification layers 331D and 331E are provided on either side of each of the modification layers 331A in terms of the x-direction, so as to be continuous with the plane S2. More specifically, it is desirable to form each of the modification layers 331D and the modification layers 331E to be positioned apart from a corresponding one of the modification layers 331A in terms of the x-direction and to be positioned as close as possible to the corresponding one of the modification layers 331A within such a range that ensures enough strength to endure manipulations during the manufacturing step. For example, the modification layer 331D is provided in substantially the same position as the position of the modification layer 331B in terms of the x-direction. Also, the modification layer 331E is provided in substantially the same position as the position of the modification layer 331C in terms of the x-direction. Further, each of the modification layers 331D and the modification layers 331E has a length L3 in the y-direction. Because the length L3 is the same as that of the modification layer 331B and the modification layer 331C, the explanation thereof will be omitted.

As explained above, the scintillator array 330 has the plurality of modification layers 331 in the regions R2 each corresponding to a position between two of the plurality of active areas 321. In other words, the plurality of modification layers 331 are not provided in the regions R1 corresponding to the active areas of the scintillator array 330 but are provided in the regions R2 each corresponding to a position between two of the active areas. The partition wall layer formed by the plurality of modification layers 331 functions as partition walls in the scintillator array 330. As a result, the scintillator array 330 realizes a structure having a high reliability in which crosstalk is inhibited.

In other words, for the purpose of preventing crosstalk, the scintillator array 330 has the plurality of modification parts that do not penetrate therethrough, in the regions each corresponding to a position between two of the plurality of active areas. More specifically, each of the modification layers 331A, 331B, 331C, 331D, and 331E is formed so as not to be continuous with at least one of the planes S1 and S2. Accordingly, each of the modification layers 331A, 331B, 331C, 331D, and 331E is formed so as not to penetrate through the scintillator in the z-direction.

For example, the plurality of modification layers 331 are provided in mutually-different positions in each of the regions R2. Further, in a lateral view, each of the modification layers 331 overlaps with at least another one of the modification layers with respect to the direction of the x-y plane. As a result, any of the lateral faces (the faces other than the plane S1 and the plane S2) of the detecting elements (the region R1) is surrounded by at least one of the modification layers. With this arrangement, even when the scintillation light 5 generated in the detected elements is scattered in the direction toward an adjacently-positioned detecting element, the scintillation light 5 is reflected by at least one of the modification layers 331. As a result, the scintillator array 330 is able to inhibit crosstalk.

In other words, in any position between the incidence plane and the exit plane in the regions each corresponding to a position between two of the active areas, the scintillator array 330 has, in a lateral view, at least one of the plurality of modification parts. In other words, as being viewed from the x-direction, in any position on a y-z plane, each of the regions R2 of the scintillator array 330 has at least one of the plurality of modification layers (the modification layers 331A, 331B, 331C, 331D, and 331E).

Accordingly, even when the scintillation light 5 generated in the regions R1 is scattered toward any of the regions R2, the scattered light will be reflected by at least one of the modification layers that are present within the regions R2. In this situation, the term "lateral view" denotes a concept that includes a view from the x-direction and a view from the y-direction in FIG. 5A.

Further, for example, the scintillator array 330 has the same pattern on a cross-sectional plane of any of the regions R2. More specifically, in the scintillator array 330, the pattern of the modification layers 331 in the region R2 on the left side of FIG. 5A is the same as the pattern of the modification layers 331 in the region R2 on the right side. As a result, even when some crosstalk occurs by some chance, the scintillator array 330 is able to reduce unevenness that may be caused by the crosstalk.

The illustrations in FIGS. 5A and 5B are merely examples, and possible embodiments are not limited to the examples illustrated in the drawings. For instance, in FIG. 5A, the example is explained in which the modification layers 331B and 331D are provided in substantially the same position in terms of the x-direction; however, possible embodiments are not limited to this example. In other words, the modification layers 331B and 331D may be provided in mutually-different positions in terms of the x-direction. It should be noted that, however, for the purpose of reserving large active areas 321 while ensuring enough strength to endure manipulations during the manufacturing step, it is desirable to provide the modification layers 331B and 331D in mutually the same position. The principle with the modification layers 331B and 331D similarly applies to the modification layers 331C and 331E. Further, the plurality of modification layers 331 included in the scintillator array 330 do not necessarily have to have the structure illustrated in the drawings and may be realized to have other structures, which will be explained later.

A manufacturing method of the detector package 300 according to the first embodiment will be explained, with reference to FIG. 6. FIG. 6 is a flowchart illustrating an example of a manufacturing method of the X-ray detector 200 according to the first embodiment. With reference to FIG. 6, an example in which laser is radiated from the top side of FIG. 5A will be explained. In the manufacturing method illustrated in FIG. 6, steps S101 to S103 correspond to a manufacturing method of the scintillator array 330.

As illustrated in FIG. 6, at step S101, the modification layers 331D and 331E are formed in the scintillator crystals. For example, within the modification layers 331D, cracks that are positioned farthest from the laser radiation position are formed first. After that, when the modification layers 331D have been formed, the modification layers 331E are formed.

In the modification layers 331E also, cracks that are positioned farthest from the laser radiation position are formed first.

At step S102, the modification layers 331A are formed in the scintillator crystals. For example, within the modification layers 331A, cracks that are positioned farthest from the laser radiation position are formed first.

At step S103, the modification layers 331B and 331C are formed in the scintillator crystals. For example, within the modification layers 331B, cracks that are positioned farthest from the laser radiation position are formed first. After that, when the modification layers 331B have been formed, the modification layers 331C are formed. In the modification layers 331C also, cracks that are positioned farthest from the laser radiation position are formed first. As a result, the scintillator array 330 has been formed.

At step S104, the scintillator array 330 is mounted on the PDA 320. For example, the scintillator array 330 is mounted on the PDA 320 by using a tool, in such a manner that the positions of the regions R1 in the scintillator array 330 are aligned with the positions of the active areas 321 in the PDA 320.

As explained above, in the method for manufacturing the detector package 300, within the scintillator crystals, the plurality of modification layers 331 are formed in the regions each corresponding to a position between two of the plurality of active areas 321 of the PDA 320. More specifically, in the method for manufacturing the detector package 300, the plurality of modification layers 331 are sequentially formed, starting with the modification layer 331 formed in the position farthest from the laser radiation position. With these arrangements, the method for manufacturing the detector package 300 has excellent yield because the manufacturing method uses the simple steps.

For example, unlike the scintillator array 330 disclosed herein, in a scintillator array having no modification layer 331, partition walls are formed by using reflective material resin. In that situation, the scintillator array is formed by performing a plurality of steps such as forming grooves in scintillator crystals and inserting and hardening a reflective material in the grooves. In contrast, the scintillator array 330 according to the first embodiment is formed by performing the laser radiation step. For this reason, the method for manufacturing the scintillator array 330 has excellent yield because the manufacturing method uses the simple step.

FIG. 6 merely illustrates an example, and possible embodiments are not limited to the example illustrated in the drawing. For example, although FIG. 6 illustrates an example in which the modification layers 331C are formed after the modification layers 331B are formed, the order may arbitrarily be changed. Further, in the method for manufacturing the detector package 300, the modification layers 331 do not necessarily have to be formed starting with the modification layers 331 positioned farthest from the laser radiation position. This situation may be addressed, as necessary, by inserting a step of changing the laser radiation direction or a step of turning over the scintillator crystals. However, to omit these steps, it is desirable to form the modification layers 331 starting with the modification layers 331 positioned farthest from the laser radiation position.

A First Modification Example of the First Embodiment

Figure 7A:
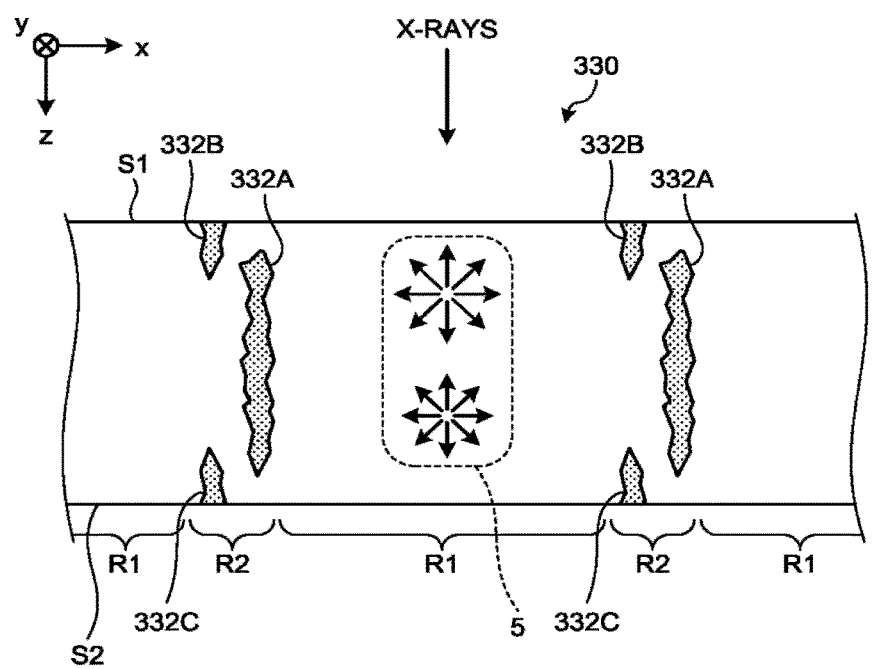

A structure of the scintillator array 330 according to a first modification example of the first embodiment will be explained, with reference to FIGS. 7A and 7B. FIGS. 7A and 7B are drawings illustrating an example of the structure of the scintillator array 330 according to the first modification example of the first embodiment. FIG. 7A illustrates a structure on an x-z cross-sectional plane of the scintillator array 330, in the xyz coordinate system of the scintillator array 330 illustrated in FIG. 4. FIG. 7B illustrates a structure of the scintillator array 330 as viewed from the y-direction, in the xyz coordinate system of the scintillator array 330 illustrated in FIG. 4. Although FIG. 7A illustrates the x-z cross-sectional plane of the scintillator array 330 as an example, a y-z cross-sectional plane of the scintillator array 330 also has the same structure. In FIG. 7A, the X-ray radiation direction is indicated by the arrow with a solid line.

As illustrated in FIGS. 7A and 7B, the scintillator array 330 has modification layers 332A, 332B, and 332C. In the following sections, when being referred to without being distinguished from each other, the modification layers 332A, 332B, and 332C will collectively be referred to as "modification layers 332".

In contrast to the scintillator array 330 illustrated in FIGS. 5A and 5B, the scintillator array 330 illustrated in FIGS. 7A and 7B do not have the modification layers 331C and the modification layers 331E. In other words, the scintillator array 330 illustrated in FIGS. 7A and 7B has the modification layers 331A, 331B, and 331D included in the scintillator array 330 illustrated in FIGS. 5A and 5B.

In this manner, the scintillator array 330 according to the first modification example of the first embodiment has, on one side of each of the modification layers 332A, a modification layer 332B that is continuous with the plane S1 and a modification layer 332C that is continuous with the plane S2. With this arrangement, in the scintillator array 330 according to the first modification example of the first embodiment, the number of rows of the modification layers 332 is two, which is decreased by one row compared to the scintillator array 330 illustrated in FIGS. 5A and 5B. As a result, in the scintillator array 330 according to the first modification example of the first embodiment, it is possible to arrange the width of each of the regions R2 smaller, compared to that in the scintillator array 330 illustrated in FIGS. 5A and 5B. Consequently, it is possible keep large each of the regions R1 corresponding to the active areas 321.

A Second Modification Example of the First Embodiment

Figure 8A:
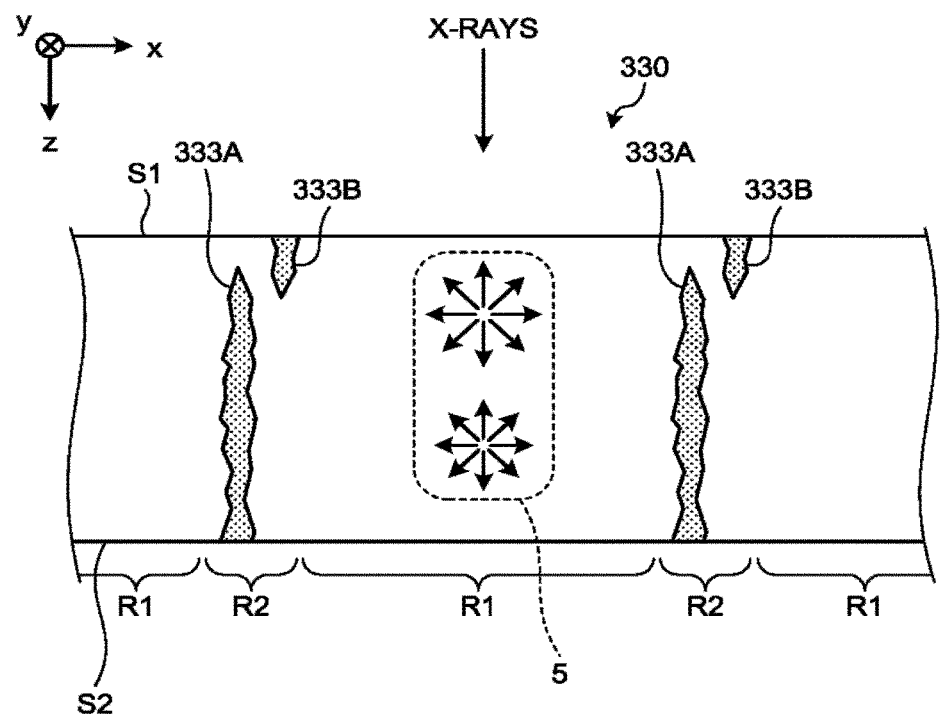

A structure of the scintillator array 330 according to a second modification example of the first embodiment will be explained, with reference to FIGS. 8A and 8B. FIGS. 8A and 8B are drawings illustrating an example of the structure of the scintillator array 330 according to the second modification example of the first embodiment. FIG. 8A illustrates a structure on an x-z cross-sectional plane of the scintillator array 330, in the xyz coordinate system of the scintillator array 330 illustrated in FIG. 4. FIG. 8B illustrates a structure of the scintillator array 330 as viewed from the y-direction, in the xyz coordinate system of the scintillator array 330 illustrated in FIG. 4. Although FIG. 8A illustrates the x-z cross-sectional plane of the scintillator array 330 as an example, a y-z cross-sectional plane of the scintillator array 330 also has the same structure. In FIG. 8A, the X-ray radiation direction is indicated by the arrow with a solid line.

As illustrated in FIGS. 8A and 8B, the scintillator array 330 has modification layers 333A and 333B. In the following sections, when being referred to without being distinguished from each other, the modification layers 333A and 333B will collectively be referred to as "modification layers 333".

The modification layers 333A and 333B are provided in mutually-different positions in each of the regions R2. Each of the modification layers 333A is provided so as to be continuous with the plane S2 and not to be continuous with the plane S1. In contrast, each of the modification layers 333B is provided so as to be continuous with the plane S1 and not to be continuous with the plane S2.

In this situation, the modification layers 333A and 333B overlap with each other in a lateral view (a view toward an x-y plane). Further, the length of each of the modification layers 333A in the z-direction is longer than that of each of the modification layers 333B. With these arrangements, the scintillator array 330 according to the second modification example of the first embodiment is able to inhibit crosstalk efficiently.

For example, it is known that, as for the scintillation light 5 occurring inside the regions R1, the closer (i.e., the shallower) the position of the occurrence of the light is to the plane S1, the stronger is the light; conversely, the closer (i.e., the deeper) the position of the occurrence of the light is to the plane S2, the weaker is the light. For this reason, the regions R2, which function as the partition wall layer, is required to inhibit crosstalk of the scintillation light 5 occurring in shallow positions.

In this situation, as for the scintillation light 5 occurring in shallow positions, although much of the light travels toward the plane S2, because the light spreads as the light gets closer to the plane S2, there is a high possibility that leakage (crosstalk) occurs in deep positions in the regions R2. For this reason, by arranging each of the modification layers 333A, which are the longest, to be continuous with the plane S2, it is possible to lower the possibility that the scintillation light 5 occurring in shallow positions may leak in deep positions. In contrast, as for the scintillation light 5 occurring in deep positions, although much of the light travels toward the plane S1, because the light spreads as the light gets closer to the plane S1, there is a high possibility that leakage occurs in shallow positions in the regions R2. However, because the scintillation light 5 occurring in the deep positions is weak, the impact of the leakage is small. Accordingly, by providing the modification layers 333B while arranging the modification layers 333A, which is the longest, so as not to be continuous with the plane S1, it is possible to realize enough strength to endure manipulations during the manufacturing step, in exchange for allowing some leakage with a small impact.

Figure 9:
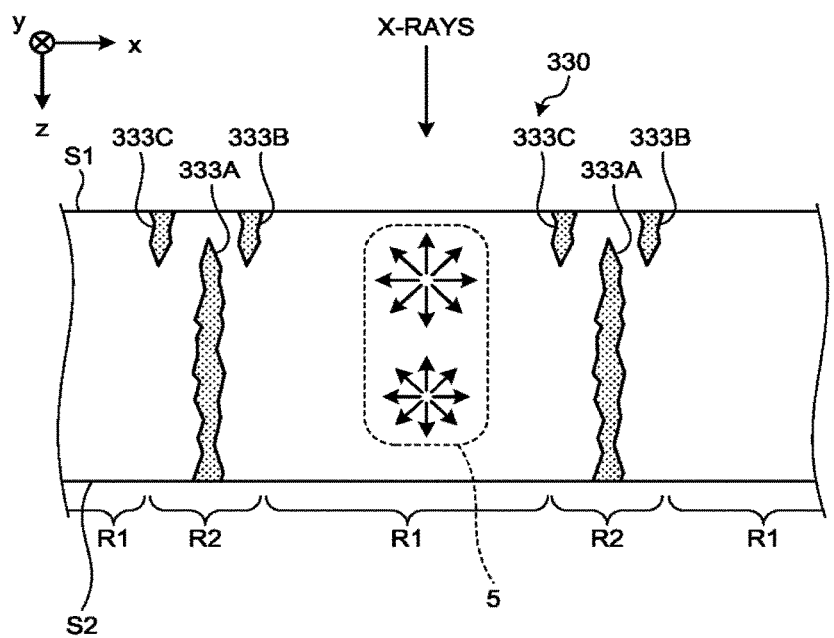
FIG. 9 is a drawing illustrating an example of a structure of a scintillator array according to a third modification example of the first embodiment.

A third modification example of the first embodiment A structure of the scintillator array 330 according to a third modification example of the first embodiment will be explained, with reference to FIG. 9. FIG. 9 is a drawing illustrating an example of the structure of the scintillator array 330 according to the third modification example of the first embodiment. FIG. 9 illustrates a structure on an x-z cross-sectional plane of the scintillator array 330, in the xyz coordinate system of the scintillator array 330 illustrated in FIG. 4. In the example illustrated in FIG. 9, modification layers 333C are added to the modification layers 333A and the modification layers 333B illustrated in FIGS. 8A and 8B. Because the structure of the scintillator array 330 illustrated in FIG. 9 as viewed from the y-direction is the same as that illustrated in FIG. 5B, the explanation thereof will be omitted.

As illustrated in FIG. 9, the scintillator array 330 has modification layers 333A, 333B, and 333C. In the following sections, when being referred to without being distinguished from each other, the modification layers 333A, 333B, and 333C will collectively be referred to as "modification layers 333". Because the modification layers 333A and 333B have the same structures as those illustrated in FIG. 8A, the explanation thereof will be omitted.

Each of the modification layers 333C illustrated in FIG. 9 is provided so as to cover both sides of a corresponding one of the modification layers 333A, together with a corresponding one of the modification layers 333B. Further, each of the modification layers 333C has, for example, approximately the same length as each of the modification layers 333B and is continuous with the plane S1. In this manner, the scintillator array 330 further has the modification layers 333C in addition to the modification layers 333A and modification layers 333B illustrated in FIGS. 8A and 8B. Consequently, it is possible to reduce crosstalk that may occur in shallow positions in the regions R2.

Figure 10A:
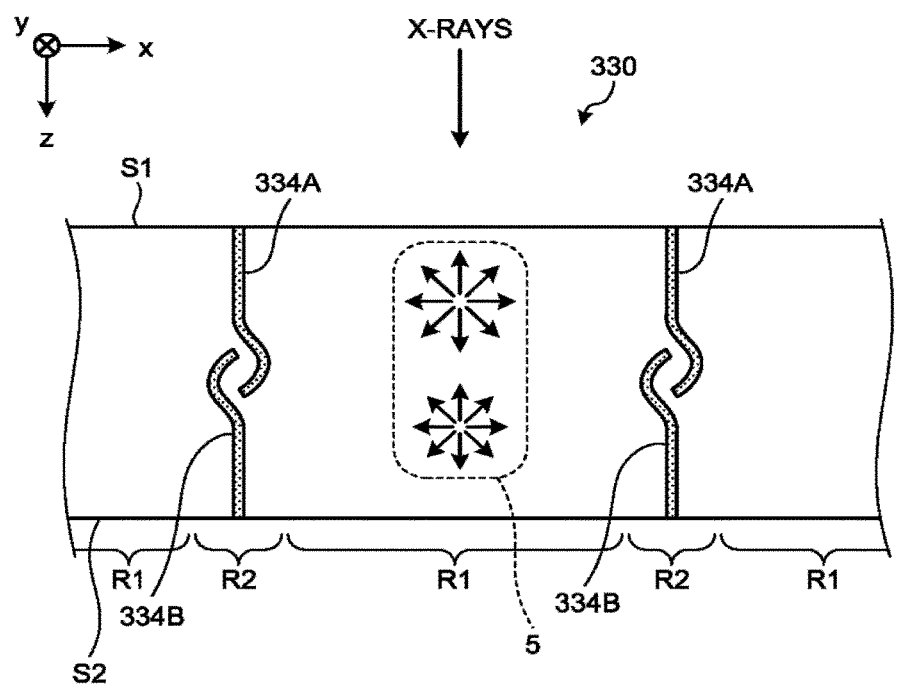

A fourth modification example of the first embodiment A structure of the scintillator array 330 according to a fourth modification example of the first embodiment will be explained, with reference to FIGS. 10A and 10B. FIGS. 10A and 10B are drawings illustrating an example of the structure of the scintillator array 330 according to the fourth modification example of the first embodiment. FIG. 10A illustrates a structure on an x-z cross-sectional plane of the scintillator array 330, in the xyz coordinate system of the scintillator array 330 illustrated in FIG. 4. FIG. 10B illustrates a structure of the scintillator array 330 as viewed from the y direction, in the xyz coordinate system of the scintillator array 330 illustrated in FIG. 4. Although FIG. 10A illustrates the x-z cross-sectional plane of the scintillator array 330 as an example, a y-z cross-sectional plane of the scintillator array 330 also has the same structure. In FIG. 10A, the X-ray radiation direction is indicated by the arrow with a solid line.

As illustrated in FIGS. 10A and 10B, the scintillator array 330 has modification layers 334A and 334B. In the following sections, when being referred to without being distinguished from each other, the modification layers 334A and 334B will collectively be referred to as "modification layers 334".

The modification layers 334A and 334B are provided in mutually-different positions in each of the regions R2. Each of the modification layers 334A is provided so as to be continuous with the plane S1 and not to be continuous with the plane S2. In contrast, each of the modification layers 334B is provided so as to be continuous with the plane S2 and not to be continuous with the plane S1.

In this situation, the modification layers 334A and the modification layers 334B are provided as being curved so as to overlap with each other in a lateral view (a view toward an x-y plane). More specifically, straight sections (the sections that are not curved) of the modification layers 334A and the modification layers 334B are provided in substantially the same position in terms of the x-direction.

However, because each of the modification layers 334A is curved in the positive direction of the x-direction, while each of the modification layers 334B is curved in the negative direction of the x-direction, the modification layers 334A and the modification layers 334B are formed so as not to be continuous with each other. With these arrangements, the scintillator array 330 according to the fourth modification example of the first embodiment is able to mitigate concentration of stress. Consequently, even though the interval between each pair made up of a modification layer 334A and a modification layer 334B is small, the scintillator array 330 is able to have enough strength to endure manipulations during the manufacturing step.

FIG. 10A illustrates the example in which the straight sections of the modification layers 334A and the modification layers 334B are provided in mutually the same position in terms of the x-direction; however, possible embodiments are not limited to this example. For instance, even when the straight sections of the modification layers 334A and the modification layers 334B are provided in mutually-different positions in terms of the x-direction, it is possible to achieve the same advantageous effects.

Figure 11A:
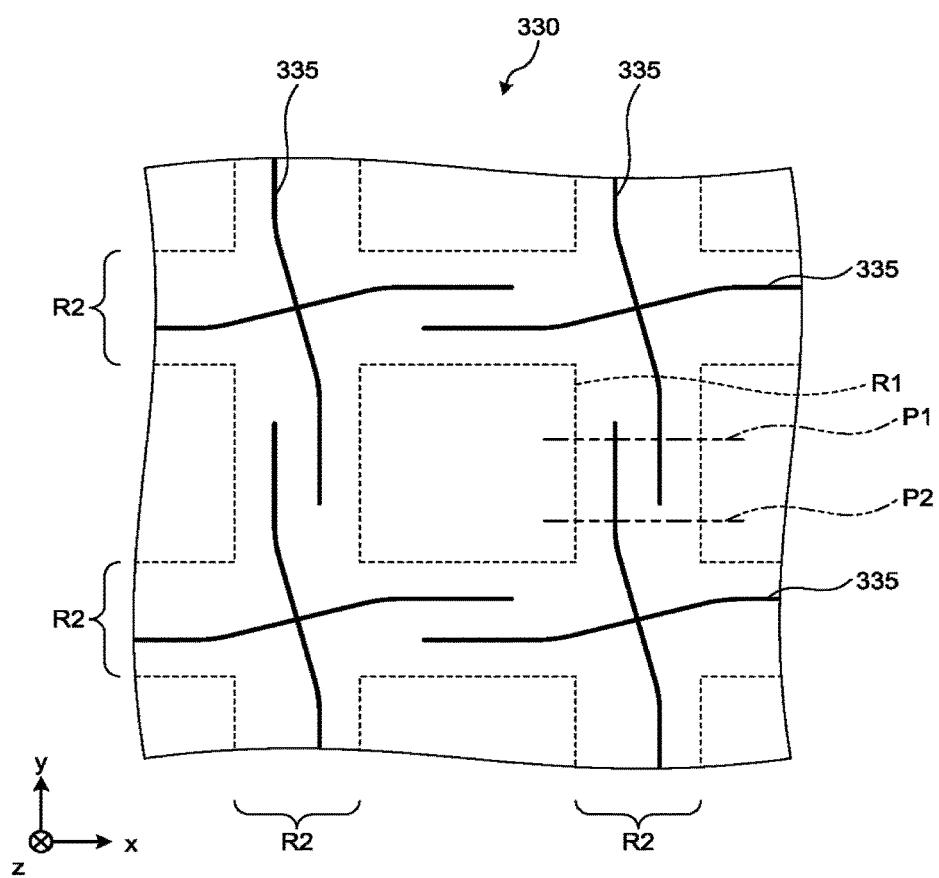
FIGS. 11A and 11C are drawings illustrating an example of a structure of a scintillator array according to a fifth modification example of the first embodiment.
Figure 11B:
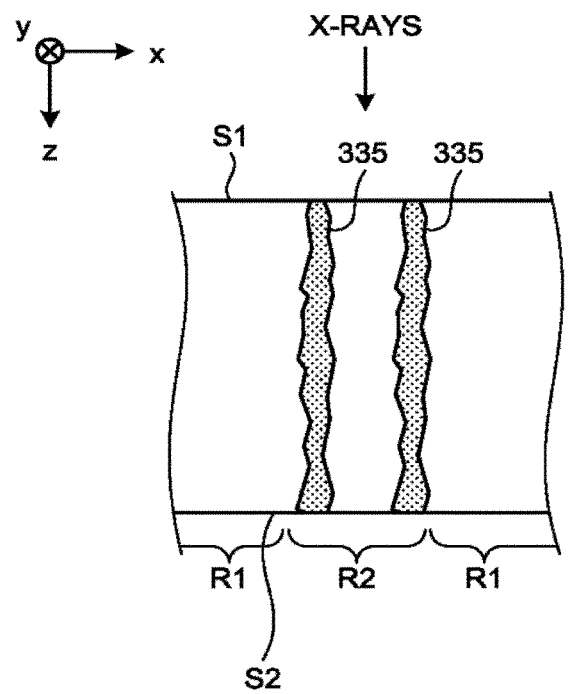
Figure 11C:
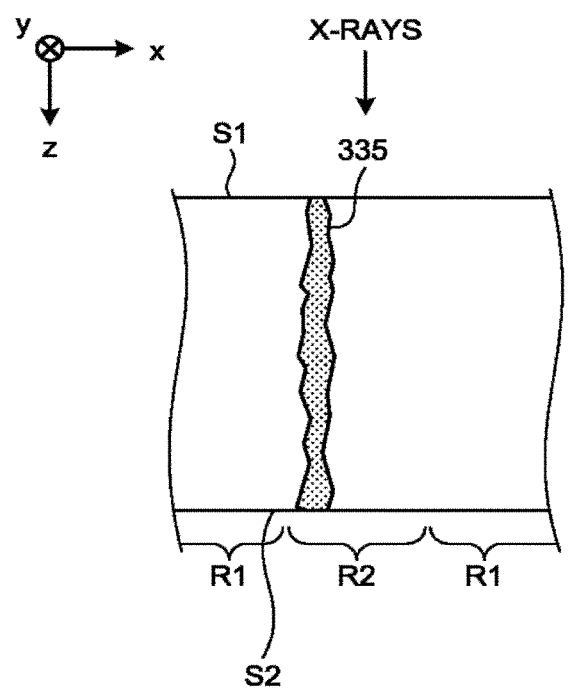

A fifth modification example of the first embodiment A structure of the scintillator array 330 according to a fifth modification example of the first embodiment will be explained, with reference to FIGS. 11A, 11B, and 11C. FIGS. 11A, 11B, and 11C are drawings illustrating an example of the structure of the scintillator array 330 according to the fifth modification example of the first embodiment. FIG. 11A illustrates a structure of the scintillator array 330 as viewed from the z-direction, in the xyz coordinate system of the scintillator array 330 illustrated in FIG. 4. FIG. 11B illustrates a structure on an x-z cross-sectional plane in the position P1 in FIG. 11A. FIG. 11C illustrates a structure on an x-z cross-sectional plane in the position P2 in FIG. 11A. Although FIGS. 11B and 11C each illustrate the x-z cross-sectional plane of the scintillator array 330 as an example, a y-z cross-sectional plane of the scintillator array 330 also has the same structure. In FIGS. 11B and 11C, the X-ray radiation direction is indicated by the arrow with a solid line.

As illustrated in FIG. 11A, the scintillator array 330 has a plurality of modification layers 335. The modification layers 335 each substantially have a cross shape in a planar view and are provided in mutually-different positions. More specifically, each of the modification layers 335 is provided in such a manner that, in a planar view, the center of the modification layer 335 substantially having the cross shape is positioned at a corresponding one of the intersections of the regions R2 that are formed in a grid formation. Further, in a lateral view, each of the modification layers 335 is continuous with the plane S1 and the plane S2.

Further, the modification layers 335 overlap with each other in terms of the direction of the x-y plane, in at least a part of the region R1 corresponding to a position between two adjacently-positioned active areas 321. For example, the x-z cross-sectional plane in the position P1 contains two modification layers 335 (FIG. 11B), whereas the x-z cross-sectional plane in the position P2 contains one modification layer 335 (FIG. 11C). This indicates that the two modification layers 335 overlap with each other in the position P1.

As explained above, in the scintillator array 330 according to the fifth modification example of the first embodiment, each of the regions R1 is covered by the plurality of modification layers 335 but is connected to the adjacently-positioned region R1 in the position P1.

Accordingly, the scintillator array 330 according to the fifth modification example of the first embodiment is able to inhibit crosstalk while having enough strength to endure manipulations during the manufacturing step.

Second Embodiment

In the first embodiment, the example is explained in which the scintillator array 330 is formed and is subsequently mounted (laminated) on the PDA 320; however, possible embodiments are not limited to this example. For instance, another arrangement is also acceptable in which after the scintillator crystals serving as materials for the scintillator array 330 are mounted on the PDA 320, the scintillator array 330 is formed by using laser.

Figure 12:
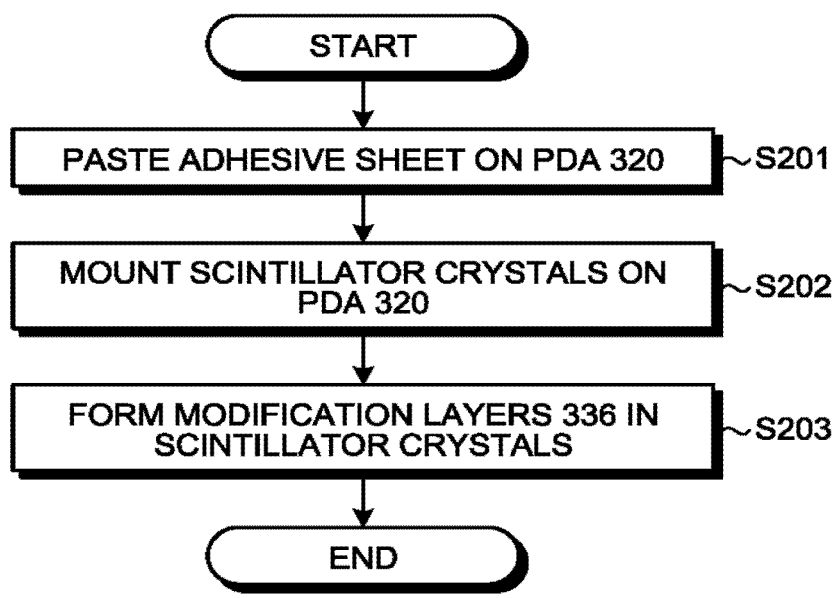
FIG. 12 is a flowchart illustrating an example of a manufacturing method of a detector package according to a second embodiment.

A method for manufacturing the detector package 300 according to a second embodiment will be explained, with reference to FIG. 12. FIG. 12 is a flowchart illustrating an example of the method for manufacturing the detector package 300 according to the second embodiment.

As illustrated in FIG. 12, at step S201, an adhesive sheet is pasted on the PDA 320. For example, a transparent adhesive sheet is pasted on the plurality of active areas 321 provided in the PDA 320.

At step S202, scintillator crystals are mounted on the PDA 320. For example, the scintillator crystals that are cut to the size of precursors for the scintillator array 330 are mounted on the PDA 320.

At step S203, modification layers 336 (see FIGS. 13A and 13B) are formed in the scintillator crystals. For example, cracks positioned to be continuous with the plane S2 are formed first, whereas cracks positioned to be continuous with the plane S1 are formed later.

Figure 13A:
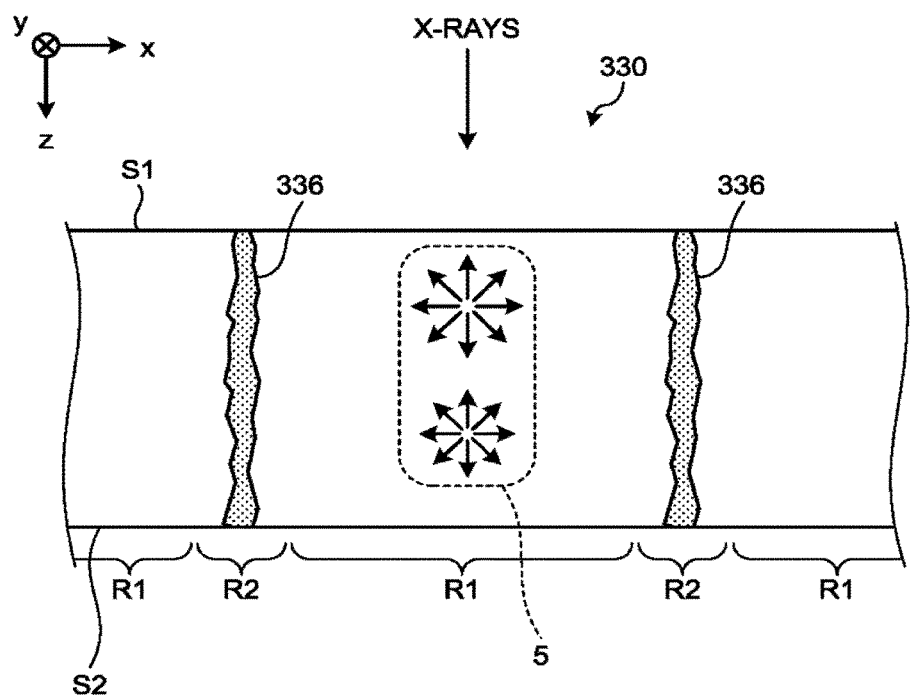
FIGS. 13A and 13B are drawings illustrating an example of a structure of a scintillator array according to the second embodiment.
Figure 13B:
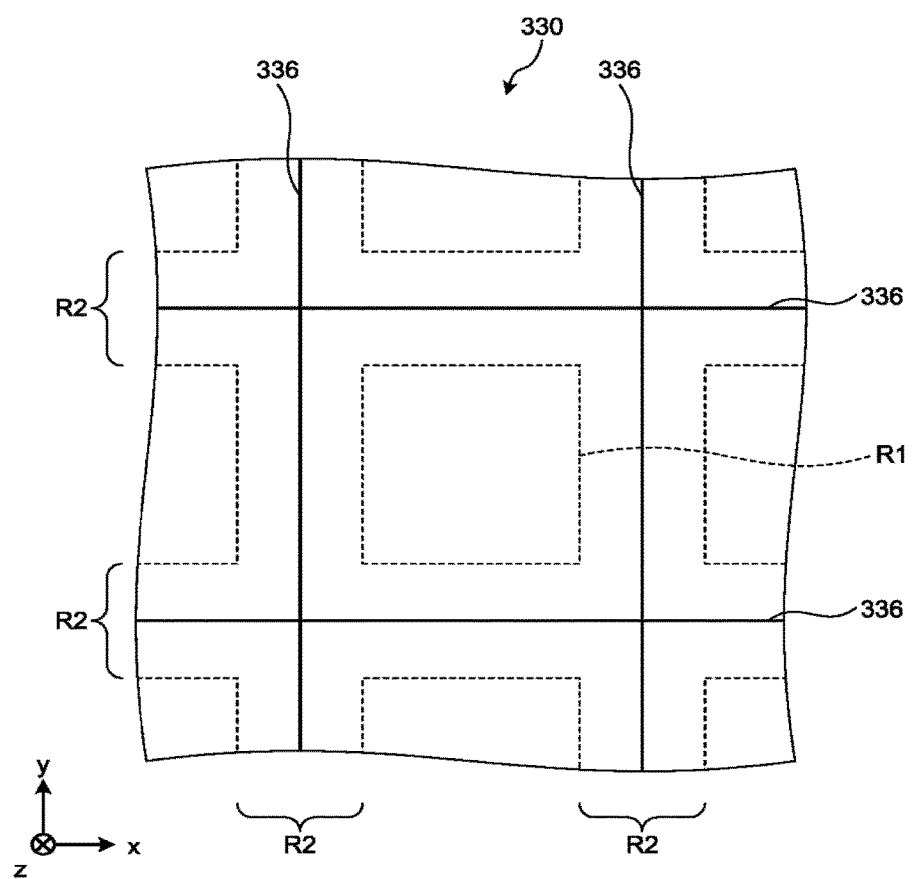

With reference to FIGS. 13A and 13B, a structure of the scintillator array 330 according to the second embodiment will be explained. FIGS. 13A and 13B are drawings illustrating an example of the structure of the scintillator array 330 according to the second embodiment. FIG. 13A illustrates a structure on an x-z cross-sectional plane of the scintillator array 330, in the xyz coordinate system of the scintillator array 330 illustrated in FIG. 4. FIG. 13B illustrates a structure of the scintillator array 330 as viewed from the z-direction, in the xyz coordinate system of the scintillator array 330 illustrated in FIG. 4. Although FIG. 13A illustrates the x-z cross-sectional plane of the scintillator array 330 as an example, a y-z cross-sectional plane of the scintillator array 330 also has the same structure. In FIG. 13A, the X-ray radiation direction is indicated by the arrow with a solid line.

As illustrated in FIGS. 13A and 13B, the scintillator array 330 has the modification layers 336. Each of the modification layers 336 is provided substantially at the center of a different one of the regions R2 in terms of the x-direction so as to be continuous with the plane S1 and the plane S2.

As explained above, according to the method for manufacturing the detector package 300 according to the second embodiment, the scintillator crystals are laminated on the PDA 320. Further, according to the method for manufacturing the detector package 300 according to the second embodiment, in the scintillator crystals, within each of the regions R2 each corresponding to a position between two of the plurality of active areas 321 of the PDA 320, a modification layer 336 is formed so as to be continuous with the plane S1 and the plane S2. With this arrangement, there is no need for the scintillator array 330 according to the second embodiment to ensure enough strength to endure manipulations during the manufacturing step. Consequently, the scintillator array 330 according to the second embodiment is able to have all the modification layers formed so as to be continuous with the plane S1 and the plane S2.

Other Embodiments

The present disclosure may be carried out in various different modes other than those in the embodiments described above.

The Detector Package

For example, the present disclosure may be realized as the detector package 300. For example, the detector package 300 includes the PDA 320 and the scintillator array 330. The PDA 320 has the plurality of active areas arranged in the grid formation. The scintillator array 330 is laminated on the PDA 320, is configured to emit light in response to incidence of X-rays thereto, and has a plurality of modification layers in the regions R2 each corresponding to a position between two of the plurality of active areas 321.

The Scintillator Array

Further, for example, the present disclosure may be realized as the scintillator array 330. For example, the scintillator array 330 is configured to emit light in response to incidence of X-rays thereto and has a plurality of modification layers in the regions R2 each corresponding to a position between two of the plurality of active areas 321 of the PDA 320.

Impregnating Modification Layers that are Continuous with a Plane with a Reflective Material Further, in the embodiments above, for instance, the example is explained in which the partition wall layer is formed only with the modification layers; however, possible embodiments are not limited to this example. For instance, it is also acceptable to impregnate modification layers that are continuous with any one of the planes, with a reflective material that is usually used as a partition wall.

For example, the modification layers 331B, 331C, 331D, and 331E illustrated in FIG. 5A may be impregnated with a reflective material. With this arrangement, it becomes easier for the scintillation light to be reflected than when the modification layers are not impregnated with the reflected material. Further, in that situation, unlike conventional impregnation of reflective materials, there is no need to perform the process of having vacuum at the time of the impregnation. Also, it is possible to realize the impregnation and the hardening in a short period of time. Consequently, it is possible to perform the manufacturing process with simpler steps than those in conventional manufacturing methods.

Further, the constituent elements of the apparatuses and the devices illustrated in the drawings in the embodiments above are based on functional concepts. Thus, it is not necessary to physically configure the constituent elements as indicated in the drawings. In other words, the specific modes of distribution and integration of the apparatuses and the devices are not limited to those illustrated in the drawings. It is acceptable to functionally or physically distribute or integrate all or a part of the apparatuses and the devices in any arbitrary units, depending on various loads and the status of use. Further, all or an arbitrary part of the processing functions performed by the apparatuses and the devices may be realized by a CPU and a computer program analyzed and executed by the CPU or may be realized as hardware using wired logic.

With regard to the processes explained in the embodiments and the modification examples described above, it is acceptable to manually perform all or a part of the processes described as being performed automatically. Conversely, by using a method that is publicly known, it is also acceptable to automatically perform all or a part of the processes described as being performed manually. Further, unless noted otherwise, it is acceptable to arbitrarily modify any of the processing procedures, the controlling procedures, specific names, and various information including various types of data and parameters that are presented in the above text and the drawings.

According to at least one aspect of the embodiments described above, it is possible to provide a radiation detector, a medical image diagnosis apparatus, a detector package, a scintillator array, a scintillator array manufacturing method, and a radiation detector manufacturing method that have high reliability.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A radiation detector comprising:
a photodiode array having a plurality of active areas arranged in a grid formation; and
a scintillator array that is laminated on the photodiode array, is configured to emit light in response to incidence of radiation thereto, and has a plurality of modification parts that do not penetrate therethrough in regions each corresponding to a position between two of the active areas, for a purpose of preventing crosstalk, the plurality of modification parts each being an aggregation of cracks.

2. The radiation detector according to claim 1, wherein the scintillator array has an incidence plane through which the radiation becomes incident thereto and an exit plane through which the light exits to the active areas, and
in any position between the incidence plane and the exit plane in the regions each corresponding to a position between two of the active areas, the scintillator array has, in a lateral view, at least one of the plurality of modification parts.

3. The radiation detector according to claim 1, wherein the modification parts are not provided in regions corresponding to the active areas of the scintillator array, but are provided in the regions each corresponding a position between two of the active areas.

4. The radiation detector according to claim 1, wherein
the plurality of modification parts are provided in mutually-different positions in each of the regions, and
in a lateral view from a direction intersecting an incidence direction of the radiation, one of the modification parts overlaps with at least another one of the modification parts.

5. The radiation detector according to claim 1, wherein the plurality of modification parts include at least one first modification part that is continuous with an incidence plane of the radiation and at least one second modification part that is continuous with an exit plane of the light.

6. The radiation detector according to claim 5, wherein the first modification part and the second modification part overlap with each other in a lateral view from a direction intersecting an incidence direction of the radiation.

7. The radiation detector according to claim 5, wherein
the plurality of modification parts further include at least one third modification part that is not continuous with the incidence plane or the exit plane,
the first modification part and the third modification part overlap with each other, in a lateral view from a direction intersecting an incidence direction of the radiation, and
the second modification part and the third modification part overlap with each other, in a lateral view from a direction intersecting the incidence direction of the radiation.

8. The radiation detector according to claim 7, wherein the first modification part and the second modification part are provided on either side of the third modification part, on a cross-sectional plane of the region taken along an incidence direction of the radiation.

9. The radiation detector according to claim 1, wherein
the plurality of modification parts include at least one first modification part that is continuous with an incidence plane of the radiation and at least one second modification part that is continuous with a plane opposite the incidence plane, and
the first modification part and the second modification part are provided as being curved so as to overlap with each other in a lateral view from a direction intersecting an incidence direction of the radiation.

10. The radiation detector according to claim 1, wherein
each of the plurality of modification parts is continuous with an incidence plane of the radiation and an exit plane of the light,
the plurality of modification parts are provided in mutually-different positions in a planar view from an incidence direction of the radiation, and
the plurality of modification parts overlap with each other in at least a part of each of the regions each corresponding to a position between two adjacently-positioned active areas.

11. A medical image diagnosis apparatus comprising:
a radiation generating device configured to generate radiation; and
a radiation detector including a photodiode array that has a plurality of active areas arranged in a grid formation and a scintillator array that is laminated on the photodiode array, is configured to emit light in response to incidence of the radiation thereto, and has a plurality of modification parts that do not penetrate therethrough, in regions each corresponding to a position between two of the active areas, for a purpose of preventing crosstalk, the plurality of modification parts each being an aggregation of cracks.

12. A detector package comprising:
a photodiode array having a plurality of active areas arranged in a grid formation; and
a scintillator array that is laminated on the photodiode array, is configured to emit light in response to incidence of radiation thereto, and has a plurality of modification parts that do not penetrate therethrough, in regions each corresponding to a position between two of the active areas, for a purpose of preventing crosstalk, the plurality of modification parts each being an aggregation of cracks.

13. A scintillator array that is configured to emit light in response to incidence of the radiation thereto and comprises a plurality of modification parts that do not penetrate trleret in a region corresponding to a position between active areas of a photodiode array, for a purpose of preventing crosstalk, the plurality of modification parts each being an aggregation of cracks.

14. A method for manufacturing a scintillator array comprising: forming, within scintillator crystals, a plurality of modification parts that do not penetrate therethrough, in a region corresponding to a position between active areas of a photodiode array, for a purpose of preventing crosstalk, the plurality of modification parts each being an aggregation of cracks.

15. The method for manufacturing the scintillator array according to claim 14, wherein the plurality of modification parts including a first part and a second part, the first part being closer to a laser, which irradiates the scintillator array to form the plurality of modification parts, than the second part, and the plurality of modification parts are sequentially formed with the first part being formed before the second part.

16. A radiation detector comprising:
a photodiode array having a plurality of active areas arranged in a grid formation; and
a scintillator array that is laminated on the photodiode array, is configured to emit light in response to incidence of radiation thereto, and has a modification part that is continuous with an incidence plane of the radiation and an exit plane of the light, in a region corresponding to a position between two of the active areas, for a purpose of preventing crosstalk, the modification part being an aggregation of cracks.

17. A method for manufacturing a radiation detector comprising:
laminating a scintillator crystal on a photodiode array; and
forming, within the scintillator crystal, a modification part that is continuous with an incidence plane of radiation and an exit plane of scintillation light, in a region corresponding to a position between active areas of the photodiode array, for a purpose of preventing crosstalk, the modification part being an aggregation of cracks.

* * * * *